United States Patent [19]

Conte, Jr. et al.

[11] 4,413,123
[45] Nov. 1, 1983

[54] SOLUTION SYNTHESIS OF 1,3,5-TRIACRYLYLHEXAHYDRO-S-TRIAZINE

[75] Inventors: Louis B. Conte, Jr., Newark; Walter T. Reichle, Warren, both of N.J.

[73] Assignee: Union Carbide Corporation, Danbury, Conn.

[21] Appl. No.: 363,108

[22] Filed: Mar. 29, 1982

[51] Int. Cl.$^3$ ............................................. C07D 251/04
[52] U.S. Cl. ..................................... 544/215; 544/193; 544/180
[58] Field of Search ....................... 544/193, 180, 215

[56] References Cited

U.S. PATENT DOCUMENTS 2,559,835  7/1981  Zerner et al. ...................... 260/248
3,518,264  6/1970  Beears ................................. 260/248
3,518,265  6/1970  Beears ................................. 260/248
3,736,320  5/1973  Karustis ............................. 260/248
3,954,750  5/1976  Coon .................................. 544/215

FOREIGN PATENT DOCUMENTS 55-40649  10/1980  Japan .

Primary Examiner—John M. Ford
Attorney, Agent, or Firm—W. E. Dickheiser

[57] ABSTRACT 1,3,5-triacrylylhexahydro-s-triazine is prepared as a solution in excess of about 10 weight percent and in yields of up to about 99 percent of theoretical by reacting acrylonitrile and trioxane with a catalytic amount of an acid having a Hammet activity function ($H_o$) in excess of about 7.3 utilizing methylene chloride as the reaction medium.

12 Claims, No Drawings

SOLUTION SYNTHESIS OF 1,3,5-TRIACRYLYLHEXAHYDRO-S-TRIAZINE

This invention relates to an improved process for the production of 1,3,5-triacrylylhexahydro-s-triazine (TAHT). Because the TAHT produced by this novel process is in solution form, it is more easily applied to inorganic fillers for use as a reinforcement promoter.

The use of 1,3,5-triacrylylhexahydro-s-triazine as a reinforcement promoter is disclosed in U.S. patent application Ser. No. 295,811 filed Aug. 27, 1981, now U.S. Pat. No. 4,385,136 (Ancker et al.) issued on May 24, 1983. Similarly, Japanese Patent Application Public Disclosure Number 133438/1980, disclosed on Oct. 17, 1980, relates to polyolefinic resin compositions containing 1,3,5-triacrylylhexahydro-s-triazine.

A major problem faced when TAHT is employed as a reinforcement promoter is that this compound is substantially insoluble in water and in many of the common organic solvents, as seen in Table I below. Therefore it is difficult to achieve uniform TAHT dispersion throughout the filler-polymer mixture. Current technology (see Japanese Disclosure 133438/1980, supra) requires that the TAHT be (1) either finely ground and mixed in a solid form with the inorganic filler or (2) suspended in water, alcohol, acetone or other organic solvent for spraying. Thus application of TAHT as a solid requires costly grinding and mixing steps as well as the use of greater amounts of expensive TAHT to ensure sufficient dispersion throughout the inorganic filler. Liquid application requires the use of large amounts of solvent with the accompanying expenses of both solvent cost and solvent removal. Thus there is an evident need for a process which would produce increased concentrations of TAHT in solution. Heretofore, TAHT has been produced by the reaction of acrylonitrile with trioxane or formaldehyde utilizing solvents in which TAHT is only minimally soluble. For example, U.S. Pat. No. 3,736,320 discloses (in Example 1) that conversions of 68% of theoretical can be achieved when benzene is employed as a solvent. U.S. Pat. No. 3,518,264 (in Example I) shows conversions of 95.8 percent of theoretical utilizing carbon tetrachloride as the reaction medium. U.S. Pat. No. 3,518,265 (in Example V) discloses that conversions of 85% of theoretical may be achieved when perchloroethylene is employed as the reaction medium.

However, as is seen in Table I below, TAHT is only about 1 weight percent soluble in aromatic hydrocarbons, such as benzene, only 0.2 weight percent soluble in perchloroethylene, and essentially insoluble in carbon tetrachloride. Thus TAHT produced using any of these solvents must either be incorporated into organic fillers as a solid or redissolved or suspended in another organic solvent, such as acetone, prior to such incorporation. Therefore, there are obvious advantages to a process therein TAHT is produced in solution form, such that it may be directly applied to inorganic fillers.

TABLE I

SOLUBILITY OF TAHT

| SOLVENT | WEIGHT % TAHT SOLUBLE AT 28° C. |
| --- | --- |
| water | approximately 0.8 |
| methanol | 4.0 |
| ethanol | 2.7 |

TABLE I-continued

SOLUBILITY OF TAHT

| SOLVENT | WEIGHT % TAHT SOLUBLE AT 28° C. |
| --- | --- |
| acetone | 6.3 |
| aliphatic hydrocarbons | .0 |
| aromatic hydrocarbons | 1 |
| $CCl_4$ | .0 |
| $CHCl_3$ | 2.9 |
| $CH_2Cl_2$ | 11–12 |
| $CCl_2CCl_2$ | 0.2 |
| $CCl_3CH_3$ | 7.7 |

It has now been found that TAHT may be prepared as a solution, in concentrations of up to about 10 weight percent or higher and in conversions of up to about 95 percent or higher of theoretical, when methylene chloride is employed as the reaction medium. This discovery was completely unexpected and unobvious in light of TAHT's relative insolubility in other chlorinated hydrocarbons such as carbon tetrachloride, chloroform, etc. (see Table I, supra).

An additional benefit of the use of methylene chloride is the reduced environmental hazards associated with this compound vis-a-vis benzene and carbon tetrachloride. The American Conference of Governmental Industrial Hygienists (A.C.G.I.H.) (1981) has set the following standards for the listed solvents:

| | TWA[1] (ppm[3]) | STEL[2] (ppm) |
| --- | --- | --- |
| benzene | 10 | 25 |
| carbon tetrachloride | 5 | 20 |
| perchloroethylene (tetrachloroethylene) | 100 | 150 |
| methylene chloride | 100 | 500 |

[1]-TWA = Threshold Limit Value - Time Weighted Average—the time-weighted average concentration for a normal 8-hour workday and a 40-hour workweek, to which nearly all workers may be repeatedly exposed, day after day, without adverse effect.
[2]-STEL = Threshold Limit Value - Short Term Exposure Limit—the maximinimal concentration to which workers can be exposed for a period up to 15 minutes continuously without suffering adverse effect.
[3]-ppm = parts per million Thus it is apparent from both an environmental and health viewpoint that methylene chloride is preferable to the solvents employed in the prior art.

DESCRIPTION OF THE INVENTION

This invention relates to a process for the production of 1,3,5-triacrylylhexahydro-s-triazine in solution form. This process involves the reaction of acrylonitrile with trioxane utilizing a catalytic amount of an acid having an active proton in a methylene chloride reaction medium. The TAHT, produced in solution of up to about 10 weight percent or higher, may be then directly applied to inorganic fillers for use as a reinforcement promoter. If desired, the acid catalyst may be separated from the solution prior to its application by means well known to one skilled in the art including distillation, addition of anhydrous bases such as potassium carbonate, sodium carbonate, calcium carbonate and the like, etc.

While not wishing to be held to any particular reaction mechanism, it is hypothesized that the production of TAHT occurs according to the following sequence. The acid catalyst first cleaves the trioxane to produce formaldehyde:

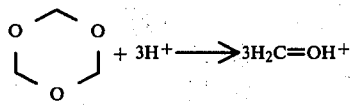

The nominally nucleophilic nitrile then attacks the aldehyde carbon to form an adduct which rearranges to form an acrolyl imide:

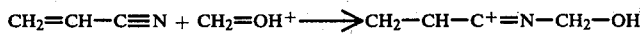

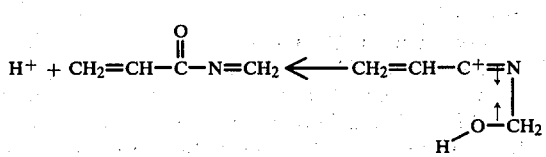

These acrylyl imides are unstable and readily trimerize to form 1,3,5-triacrylylhexahydro-s-triazine (TAHT).

The amount of trioxane charged should be such that, after decomposition of the trioxane into formaldehyde, the ratio of moles formaldehyde: moles acrylonitrile is from 1:2 to about 2:1. Preferably the ratio of moles formaldehyde: moles acrylonitrile should be slightly in excess of 1:1; i.e., from about 1.01:1 to about 1.1:1. In addition, formaldehyde may be employed in place of trioxane.

The methylene chloride solvent may be present in any amount but, for commercial practicality, one prefers to produce as concentrated a TAHT solution as possible. In addition, it should be noted that TAHT has been found to be soluble in concentrations up to about 35-40 weight percent in methylene chloride which has been heated to about 85° C. However, much of this TAHT will fall out of solution when the methylene chloride is cooled to room temperature, thus resulting in the formation of a TAHT solution with a concentration of about 10 weight percent and a crystalline TAHT precipitate. This may be a desirable method of producing solid TAHT, or, depending upon the circumstances, one may wish to employ sufficient quantities of methylene chloride in the instant process such that all the TAHT produced remains in solution.

The acid catalyst which may be employed are those with a Hammet acidity function[1] ($H_o$) in excess of about 7.3. Representative of such acids are concentrated sulfuric acid, oleum and the like. Concentrated sulfuric acid is the preferred catalyst. The acid should be present in amounts sufficient to catalyze the reaction. It has been found that the reaction rate may be increased by the periodic addition of more catalyst during the reaction and immediately after the end of the physical addition of acrylonitrile and trioxane.

[1]An explanation and listing of $H_o$ values is found in The Chemist's Companion, Arnold J. Gordon and Richard A. Ford, Wiley-Interscience.

In order to minimize the formation of methylene-bisamides, it is preferable to add a moisture scavenger and to keep reaction conditions as anhydrous as possible. Compounds well known to one skilled in the art, including organic anhydrides such as acetic anhydride and the like as well as inorganic anhydrides such as sulfur trioxide (in the form of oleum), phosphoric anhydride and the like, may be employed as the moisture scavenger. In addition, it is preferable to pretreat the methylene chloride, e.g. by drying over a molecular sieve, in order to reduce its water content.

Further, it is also preferable to add small amounts of polymerization inhibitor to the reaction mixture in order to minimize polymer formation. Polymerization inhibitors well known to one in the art, such as, for example, hydroquinone, acetonphenone, o-nitroaniline, m-nitroaniline, p-nitroaniline, n-nitroanisol, anthracene, diazoaminobenzene, o-dinitrobenzene, m-dinitrobenzene, 1,3,5-trinitrobenzene, benzophenone, p-benzoquinone, benzoyl chloride, diphenyl and the like may be employed. The amounts of moisture scavenger and polymerization inhibitor which may be added are not critical, and in general, are limited only to the extent that the presence of these compounds interferes with the production of the TAHT.

The reaction is conducted at a temperature of from about 40° C. to about 130° C. with preferred temperatures ranging from about 60° C. to about 85° C.

The reaction is conducted at pressures of from about atmospheric (i.e., about 14.5 psi) to about 1000 psi with pressures of from about 25 psi to about 75 psi $CH_2Cl_2$ preferred.

Reaction time is not critical, and may vary from less than a few hours to several days or more depending upon the reaction batch size, temperature, pressure, etc. selected. However, it is preferable to conduct the reaction as quickly as heat removal (from the exotherm produced by the reaction of acrylonitrile with trioxane) allows.

The instant process may be conducted in a batch, semicontinuous, or continuous fashion by means apparent to one skilled in the art. It is preferable to periodically (if a continuous or semicontinuous mode is selected) or after each batch is complete (if a batch type mode is selected) to wash the apparatus with hot methylene chloride in order to minimize byproduct buildup on the walls of the reactor.

It should be noted that the reaction of acrylonitrile with trioxane is exothermic. Thus, in order to control this exotherm, it is preferable to add a solution containing trioxane and acrylonitrile to a solution containing the acid catalyst at a rate low enough so that the heat produced may be removed through cooling coils or other means before such exotherm interferes with the reaction.

EXAMPLES

The following Examples serve to further illustrate the invention. They are not intended to limit the invention in any way.

A series of runs was carried out as follows.

Prior to the preparation of the TAHT solution a one-gallon stainless steel pressure reactor equipped with a stirrer, thermometer, heated jacket, and internal cooling coils, was cleaned thoroughly and then dried by heating to 80°-90° C. while purged with a dry nitrogen stream.

The reactor was charged with 3340 g (2520 ml) of methylene chloride (which had previously been dried over heat activated 4-A type molecular seives), 2 ml. of acetic anhydride and sulfuric acid (in the amounts indicated for each run in Table II) (concentration 96%). The reactor was sealed and heated to 80°-82° C.

The heat was turned off and a solution consisting of 256 g (4.83 moles) sieve dried acrylonitrile containing 0.1 weight percent hydroquinone and 149 g (1.61 moles) trioxane (containing 0.2 weight percent water) was pumped via a metering pump into the reactor at the rate of about 15 ml/min. The exotherm produced by the addition of this solution was controlled by circulating water through the internal cooling coil within the reactor.

The acrylonitrile-trioxane solution was added over a 30-40 minute period. The reaction was kept at 80°-82° C. for the additional period of time listed in Table II, below. At the end of this time, the reaction was cooled to 25°-30° C. and discharged into one-gallon glass bottles. About 0.4 g of hydroquinone (equal to about 0.1 weight percent based upon the TAHT concentration in the product) was added to the reaction product. The TAHT solution was nearly water-white and somewhat cloudy. The solids were recovered from this solution by evaporation. The amounts recovered are listed in Table II below.

TABLE II

| Example | $H_2SO_4$ (mls) | Reaction Temp. (°C.) | Conditions Pressure (psi) | Time (hours) | Solids[1] | % Conversion[2] |
|---|---|---|---|---|---|---|
| 1 | 3.8 | 75 | 30-35 | 2.0 | 10.5 | 97.3 |
| 2 | 3.8 | 80 | 35-40 | 2.0 | 9.8 | 92.6 |
| 3 | 3.8 | 75 | 30-35 | 3.0 | 10.8 | 96.1 |
| 4 | 3.8 | 80 | 35-40 | 3.0 | 10.5 | 99 |
| 5 | 3.8 | 80 | 45 | 4.0 | 9.14 | 88.9 |
| 6 | 4.8 | 80 | 45-50 | 3.0 | 10.1 | 96.0 |
| 7 | 5.0 | 80 | 45-50 | 4.0 | 9.0 | 85.6 |
| 8 | 6.8 | 80 | 45-55 | 3.0 | 10.0 | 94.3 |
| 9 | 8.0 | 80 | 35-45 | 3.5 | 9.7 | 91.5 |

[1] weight percent TAHT in product
[2] based on theoretical conversion of 3 acrylonitrile + 1 trioxane = 100%

The above data indicates that conversion as high as 99 percent of theoretical and TAHT-solvent concentration as high as 10.8 weight percent can be achieved utilizing methylene chloride as the reaction medium.

What is claimed is:

1. A process for producing 1,3,5-triacrylylhexahydro-s-triazine comprising reacting acrylonitrile and trioxane in contact with a catalytic amount of an acid having a Hammet activity function ($H_o$) in excess of about 7.3 utilizing methylene chloride as the reaction medium.

2. The process of claim 1 wherein the ratio of moles acrylonitrile to moles formaldehyde produced by the decomposition of the trioxane is from about 1:2 to about 2:1.

3. The process of claim 2 wherein the ratio of moles acrylonitrile to moles formaldehyde produced by the decomposition of the trioxane is from about 1:1.01 to about 1:1.1.

4. The process of claim 1 wherein the acid employed is sulfuric acid.

5. The process of claim 1 wherein the reaction is conducted at a temperature of from about 40° to about 130° C.

6. The process of claim 5 wherein reaction is conducted at a temperature of from about 60° to about 85° C.

7. The process of claim 1 wherein the reaction is conducted at a pressure of from about 14.5 to about 1000 psi.

8. The process of claim 1 wherein a moisture scavenger is also present.

9. The process of claim 1 wherein a polymerization inhibitor also present.

10. A process of producing 1,3,5-triacrylhexahydro-s-triazine comprising reacting acrylonitrile and trioxane in contact with a catalytic amount of sulfuric acid utilizing methylene chloride as the reaction medium, wherein there is also present hydroquinone as s polymerization inhibitor and acetic anhydride as a moisture scavenger.

11. The process of claim 8 wherein the ratio of moles acrylonitrile to moles formaldehyde produced by the decomposition of trioxane is from about 1.1.01 to about 1:1.1.

12. A process for producing 1,3,5-triacrylylhexahydro-s-triazine comprising reacting acrylonitrile with formaldehyde with a catalytic amount of sulfuric acid utilizing methylene chloride as the reaction medium.

* * * * *